United States Patent
Usuki

(10) Patent No.: US 10,280,143 B1
(45) Date of Patent: May 7, 2019

(54) PROCESS FOR PREPARING DEUTERATED DESMOSINE AND DERIVATIVES THEREOF

(71) Applicant: SOPHIA SCHOOL CORPORATION, Tokyo (JP)

(72) Inventor: Toyonobu Usuki, Tokyo (JP)

(73) Assignee: SOPHIA SCHOOL CORPORATION, Tokyo (JP)

( * ) Notice: Subject to any disclaimer, the term of this patent is extended or adjusted under 35 U.S.C. 154(b) by 0 days.

(21) Appl. No.: 15/810,634

(22) Filed: Nov. 13, 2017

(51) Int. Cl.
C07B 59/00 (2006.01)
C07D 213/55 (2006.01)

(52) U.S. Cl.
CPC .......... *C07D 213/55* (2013.01); *C07B 59/002* (2013.01); *C07B 2200/05* (2013.01)

(58) Field of Classification Search
None
See application file for complete search history.

(56) References Cited

PUBLICATIONS

Ma et al, Analytical Biochemistry, vol. 440, No. (2), pp. 158-165 (Year: 2013).*
Toyonobu Usuki et al "Total synthesis of COPD biomarker desmosine that crosslinks elastin", The Royal Society of Chemistry; Jan. 2012, pp. 3233-3235, vol. 48.
Hiroto Yanuma et al. "Total synthesis of the COPD biomarker desmosine via Sonogashira and Negishi cross-coupling reactions"; Tetrahedron; 2012, pp. 5920-5922, vol. 53.
Li-Bing Yu et al. "Lanthanide-Promoted Reactions of Aldehydes and Amine Hydrochlorides in Aqueous Solution. Synthesis of 2,3-Dihydropyridinium and Pyridinium Derivatives", J. Org Chem, 1997, vol. 62, pp. 208-211.
Daisuke Watanabe et al. "Synthesis of desmosine-$d_4$: Improvement of isotopic purity by D-H exchange of amino groups", Tetrahedron Letters, 2017, pp. 1194-1197, vol. 58.
Watanabe et al., "Synthesis of deuterium-labeled desmosine for isotope dilution LC-MS/MS analysis of COPD biomaker", presented at 6CSJ Chemistry Festa, Nov. 14, 2016, P2-084, 1 page.

* cited by examiner

*Primary Examiner* — Zinna Northington Davis
(74) *Attorney, Agent, or Firm* — Sughrue Mion, PLLC

(57) ABSTRACT

There is provided a process for preparing a compound represented by the following general formula (1) or a salt thereof, which comprises exchanging one or more of an amino proton in a compound represented by the following general formula (2) or a salt thereof to deuterium, and after the exchanging, converting a deuterium-exchanged compound of the compound represented by the general formula (2) or a salt thereof into the compound represented by the general formula (1) or a salt thereof:

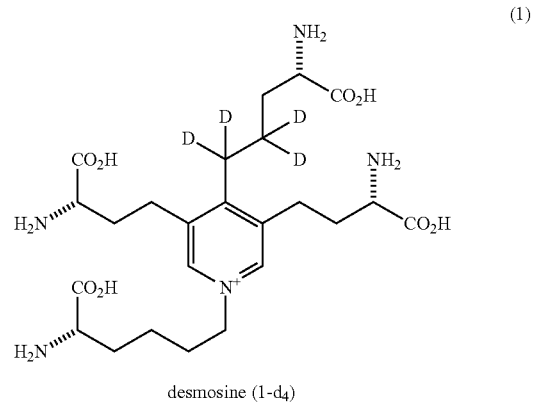

desmosine (1-$d_4$)

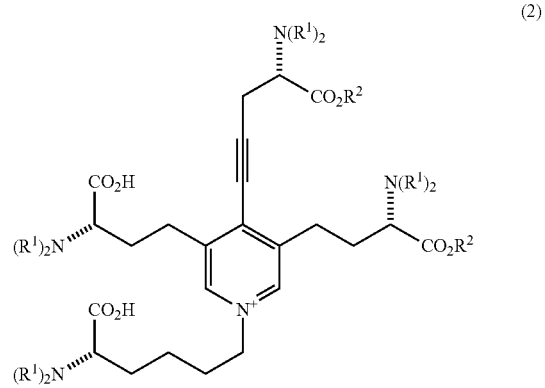

wherein, in the general formula (1), one, or two or more of hydrogen atom may be substituted with their isotope; and in the general formula (2), each of $R^1$ is independently hydrogen atom, tert-butyloxycarbonyl group or benzyloxycarbonyl group, and $R^2$ is independently tert-butyl group, benzyl group, methyl group or ethyl group.

13 Claims, No Drawings

PROCESS FOR PREPARING DEUTERATED DESMOSINE AND DERIVATIVES THEREOF

TECHNICAL FIELD

The present invention relates to a process for preparing a deuterated desmosine and derivatives thereof.

BACKGROUND ART

Chronic Obstructive Pulmonary Disease (COPD) is a generic designation of diseases such as bronchitis and pulmonary emphysema. According to the World Health Organization (WHO), currently it ranks the fourth place of the cause of death. Concerning the COPD, a root pathological condition thereof is extremely complicated and contains large majority of unknown clinical states, and even radical therapeutic agent does not exist. In this century, it is feared to rapidly increase the number of the COPD patients on a global scale due to increased number of smokers and atmospheric pollutions caused by industrial developments in developing countries, and therefore an establishment of a rapid and simple detection method becomes an overarching imperative.

Hydrolytic processing of sputum, blood, urine of a COPD patient is conducted and the obtained samples are analyzed with Liquid Chromatography-Tandem Mass Spectrometry (LC-MS/MS) to provide observations of desmosine, which serves as a crosslinking amino acid of an elastic fiber elastin controlling an expansion and a contraction of a lung alveolus and is represented by the following formula (5), and isodesmosine, which is an isomer thereof and is shown in the following formula (6). Desmosines are expected as promising biomarkers for COPD, since the quantity thereof existing in a COPD patient is distinctive as compared with that of a healthy person.

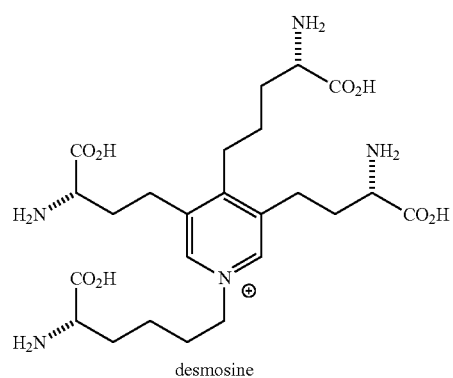

desmosine (5)

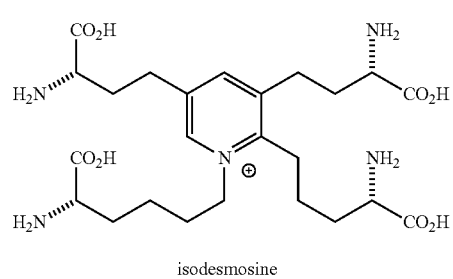

isodesmosine (6)

Technologies related to a total synthesis of desmosine are described in Toyonobu Usuki, and other 7 authors, "Total synthesis of COPD biomarker desmosine that crosslinks elastin", Chem. Commun., 2012, Vol. 48, pp. 3233 to 3235, and, Hiroto Yanuma, and another author, "Total synthesis of the COPD biomarker desmosine via Sonogashira and Negishi cross-coupling reactions", Tetrahedron Lett., 2012, Vol. 53, pp. 5920 to 5922.

Technology related to a synthetic process of compounds having pyridine ring is described in Li-Bing Yu and other 4 authors, "Lanthanide-Promoted Reactions of Aldehydes and Amine Hydrochlorides in Aqueous Solution. Synthesis of 2,3-Dihydropyridinium and Pyridinium Derivatives", J. Org. Chem., 1997, Vol. 62, pp. 208 to 211.

SUMMARY

The present invention is to provide a novel process for stably preparing a deuterated desmosine or derivatives thereof with reduced number of process steps.

According to one aspect of the present invention, there is provided a compound represented by the following general formula (1) or a salt thereof:

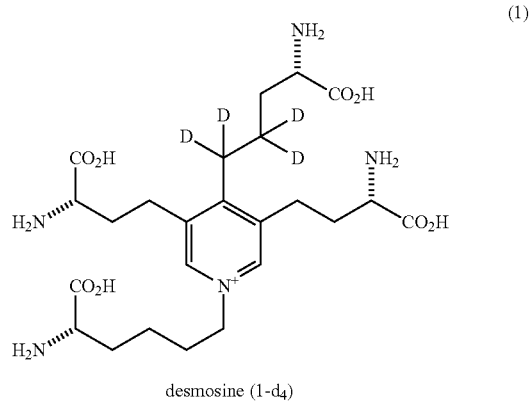

desmosine (1-d$_4$)

(wherein, in the general formula (1), one, or two or more of hydrogen atom may be substituted with their isotope), the process comprising exchanging one or more of an amino proton in a compound represented by the following general formula (2) or a salt thereof to deuterium:

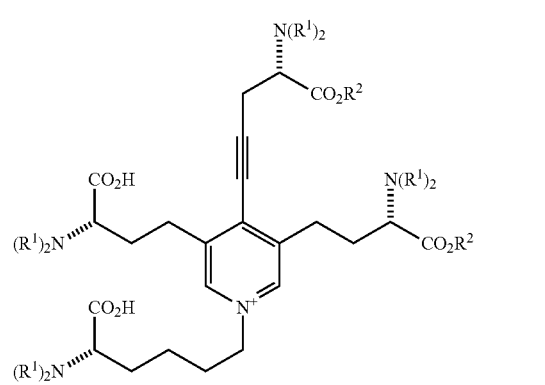

(wherein, in the general formula (2), each of $R^1$ is independently hydrogen atom, tert-butyloxycarbonyl group or benzyloxycarbonyl group, and $R^2$ is independently tert-butyl group, benzyl group, methyl group or ethyl group), and after the exchanging, converting a deuterium-exchanged compound of the compound represented by the general formula (2) or a salt thereof into the compound represented by the general formula (1) or a salt thereof.

DESCRIPTION OF EMBODIMENTS

Embodiments of the present invention will be described below, in reference with specific examples. It would be understood that a combination of specific forms described in a plurality of embodiments may be employed.

The present embodiment relates to a process for preparing a compound represented by the following general formula (1).

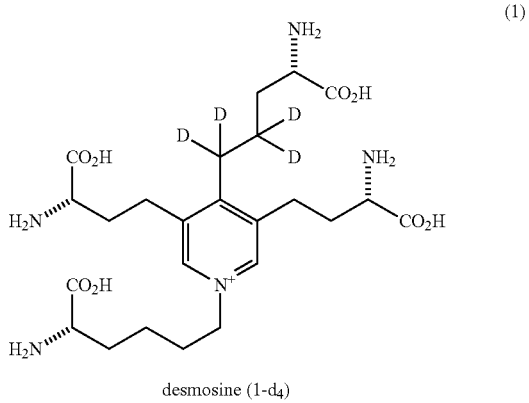

desmosine (1-d$_4$)

(Wherein, in the general formula (1), one, or two or more of hydrogen atom may be substituted with their isotope.)

In the present embodiment, the preparation process of the compound represented by the following general formula (1) includes process steps I and II. The process step I is to exchange one or more of an amino proton presented in a side chain of a precursor or a derivative of desmosine to deuterium. The process step II is deuterium addition reaction to a carbon-carbon triple bond presented in 4-position side chain of a precursor or a derivative of desmosine. An order of carrying out the process steps I and II is not limited.

More specifically, the preparation process in the present embodiment includes the following process steps.

Process Step 1: a process step for exchanging one or more of an amino proton in a compound represented by the following general formula (2) or a salt thereof to deuterium.

(Wherein, in the general formula (2), each of $R^1$ is independently hydrogen atom, tert-butyloxycarbonyl group or benzyloxycarbonyl group, and $R^2$ is independently tert-butyl group, benzyl group, methyl group or ethyl group.)

Process Step 2: after the process step 1, converting a deuterium-exchanged compound of the compound represented by the general formula (2) or a salt thereof into the compound represented by the general formula (1) or a salt thereof.

First of all, a specific configuration of the general formula (2) will be described.

In the general formula (2), $R^1$ is independently hydrogen atom, tert-butyloxycarbonyl group or benzyloxycarbonyl group. $R^1$ other than hydrogen atom is preferably tert-butyloxycarbonyl (referred to also as "Boc") group. When two or more $R^1$ other than hydrogen atom are presented in the general formula (2), while two or more $R^1$ other than hydrogen atom may be the same or may be different, these may preferably be of the same group, and more preferably all of $R^1$ other than hydrogen atom are Boc group.

In the general formula (2), $R^2$ is independently tert-butyl (referred to also as "tBu") group, benzyl (referred to also as "Bn") group, methyl group or ethyl group, preferably tBu group or Bn group and more preferably tBu group. While two or more $R^2$ may be the same or may be different, these may preferably be of the same group, and more preferably all of $R^2$ are tBu group or Bn group and further more preferably all of $R^2$ are tBu group.

Also, it is preferable in view of shortening the process step in the process step 2 as described later to be configured that $R^1$ other than hydrogen atom and $R^2$ are groups which are removable in the same process step. More specifically, it is preferable to assign Boc group for $R^1$ and to assign tBu group for $R^2$ in the general formula (2). This allows deprotecting $R^1$ and $R^2$ in a single step in the process step 2.

The compound represented by the general formula (2) is preferably the compound represented by the following formula (3) or (4).

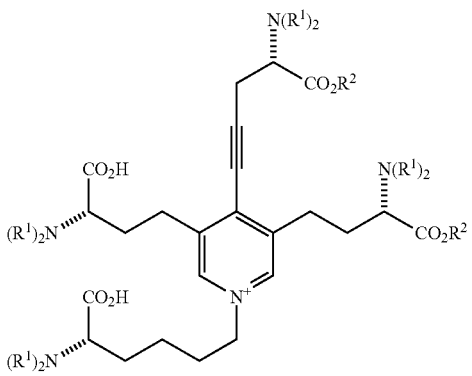

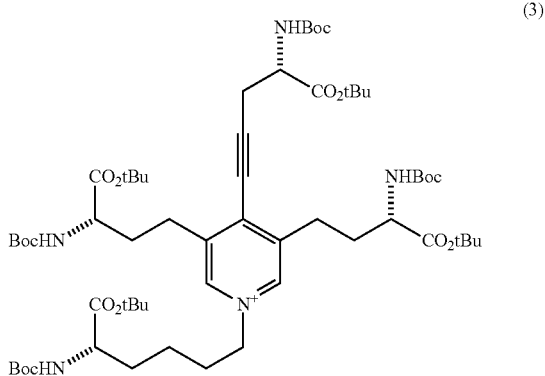

-continued

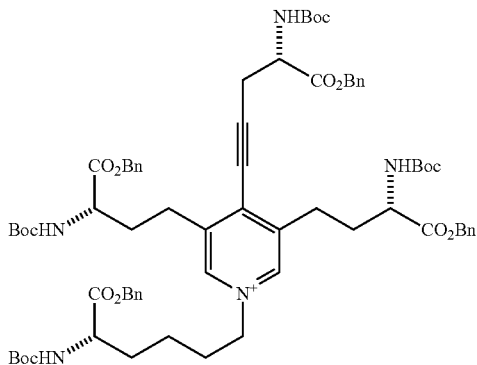

(4)

The compound represented by the general formula (2) or a salt thereof may be synthesized by using known method. Specific examples of synthesis will be described below in Examples.

Next, the process step 1 will be described.

In the process step 1, one or more hydrogen atom which binds directly to a nitrogen atom in a side chain of pyridine ring, that is, a hydrogen atom in $R^1$ is exchanged to deuterium atom. By this D-H exchange step of the amino proton, the deuterium-exchanged compound is provided.

The process step 1 preferably includes one or more cycle of dissolving the compound represented by the general formula (2) in a solvent containing deuterated polar protic solvent and removing the solvent, more preferably includes two or more of the cycles, even more preferably includes three or more of the cycles.

Specific example of the deuterated polar protic solvent includes deuterated water ($D_2O$), deuterated alcohol such as deuterated methanol, deuterated ethanol, deuterated isopropanol and the like.

The solvent preferably contains, and more preferably is deuterated methanol.

In the cycle, the dissolution of the compound represented by the general formula (2) may be carried out with stirring.

In the cycle, the removal of the solvent is carried out preferably under a reduced pressure and more preferably in vacuo.

A temperature of the D-H exchange step may be higher than a freezing point of the solvent, and is preferably equal to or higher than 5 degrees C. and more preferably equal to or higher than 10 degrees C. On the other hand, the temperature of the D-H exchange step may be lower than a boiling point of the solvent, and is preferably equal to or higher than 60 degrees C. and more preferably equal to or higher than 40 degrees C. The D-H exchange step may be carried out at room temperature (namely 25 degrees C., and hereinafter using this temperature).

In the next, the process step 2 will be described.

In the process step 2, the deuterium-exchanged compound of the compound represented by the general formula (2) or a salt thereof is converted into the compound represented by the general formula (1) or a salt thereof. More specifically, in the process step 2, a deuterium addition reaction to a carbon-carbon triple bond presented in 4-position side chain of the deuterium-exchanged compound of the compound represented by the general formula (2) or a salt thereof is carried out.

The process step 2 may include reducing the deuterium-exchanged compound or a salt thereof by a catalytic reduction and preferably by the reduction with deuterium gas and palladium carbon to obtain a reduced compound.

The conditions of the catalytic reduction is set as, for example, Pd/C concentration of 1 mol/% to 10000 mol/%, preferably 100 mol/% to 1000 mol/%.

A temperature of the catalytic reduction is set as, for example, 0 degrees C. to 100 degrees C., and preferably at room temperature.

A reaction time can be determined according to the reaction temperature, a stirring efficiency and the like, and may be, for example, determined as ranging from 12 hours to 10 days, preferably 24 hours to 8 days, more preferably 5 to 7 days.

A type of the solvent used for the catalytic reduction is not particularly limited so far as it is stable under the reactive conditions and does not inhibit the target reaction, and may be, for example, one, two or more selected from the group consisting of a deuterated water, a deuterated alcohol.

Among them, a deuterated alcohol is preferably applied. Specific example of the deuterated alcohol includes deuterated methanol, deuterated ethanol, deuterated isopropanol and the like. The reaction solvent preferably contains, and more preferably is deuterated methanol.

When one or more of $R^2$ in the general formula (2) is Bn group, the Bn group is removed by the reduction with deuterium gas and palladium carbon.

Also, the process step 2 may further include deprotecting carboxy group or amino group of the reduced compound of the deuterium-exchanged compound or a salt thereof.

For example, when one or more of $R^1$ are Boc group, or one or more of $R^2$ is tBu group, an acid treatment with an aqueous solution of trifluoroacetic acid (TFA) may be conducted to remove tBu group or Boc group. The conditions of the acid treatment is set as, for example, TFA/water=95/5, at room temperature, for 2 hours.

Through the above-described process steps, the compound represented by the general formula (1) or a salt thereof is obtained. Here, in the general formula (1), one, or two or more of hydrogen atom may be substituted with their isotope. For example, one or more of hydrogen atom other than those deuterated in the process step 2 may further be deuterated.

According to the present embodiment, a novel process for stably preparing a deuterated desmosine or derivatives thereof with reduced number of process steps. Also, according the present embodiment, a compound that can be used as a COPD biomarker is stably obtainable.

EXAMPLES

In this following experimental example, the compound represented by the general formula (1) was synthesized by a process represented by the following Schemes 1 to 3.

Scheme 1. Synthesis of iodo amino acid 6.

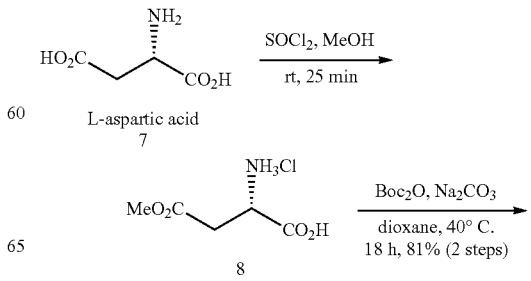

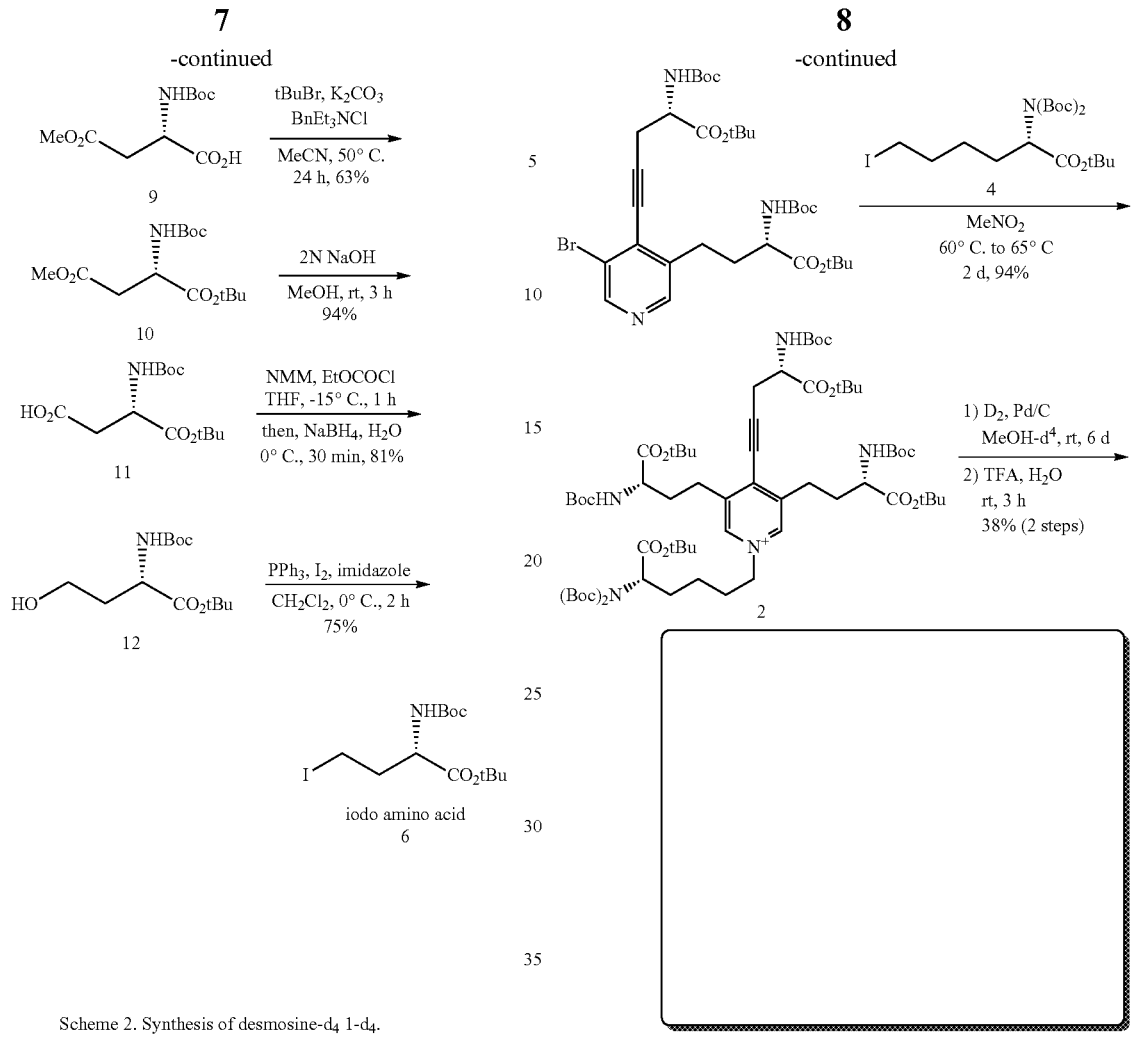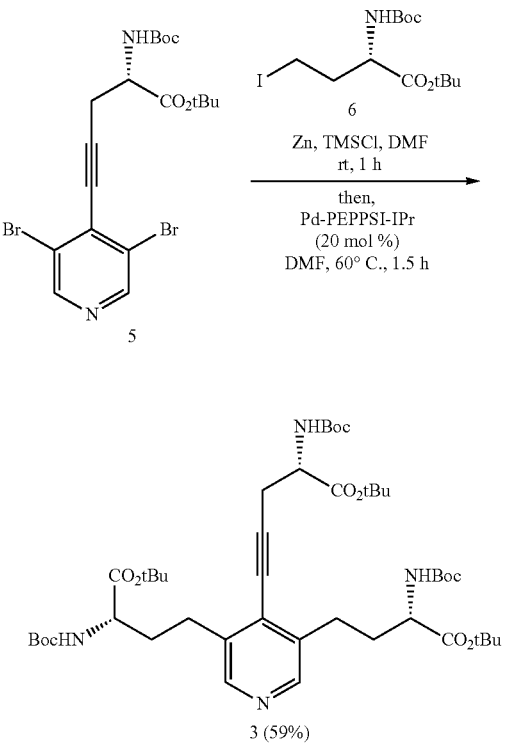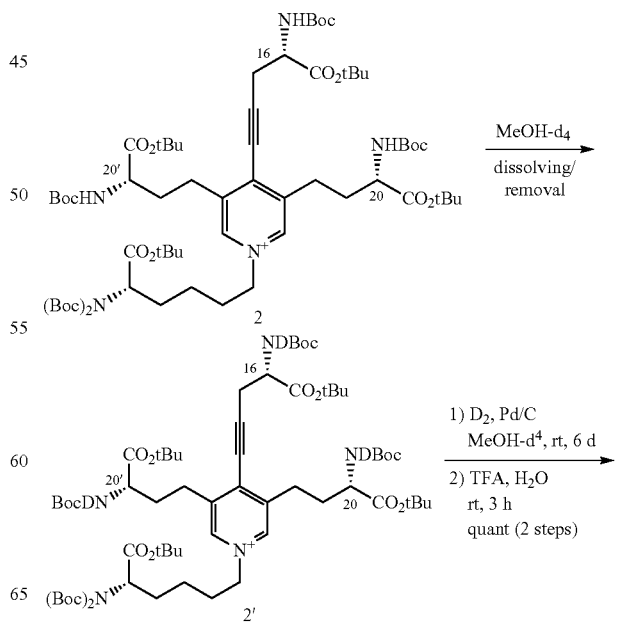

-continued

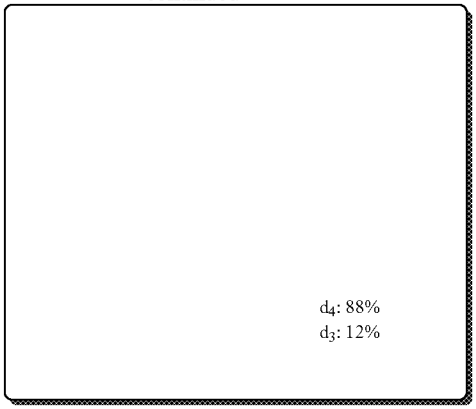

d4: 88%
d3: 12%

(General Procedures)

All non-aqueous reactions were conducted under an atmosphere of nitrogen with magnetic stirring using freshly distilled solvents unless otherwise indicated. DMF was dried by distillation and stored over activated molecular sieves. Dehydrated MeOH was purchased from Kanto Chemicals (Tokyo, Japan). All reagents were obtained from commercial suppliers and used without further purification unless otherwise stated. Analytical thin layer chromatography (TLC) was performed on Silica gel 60 $F_{254}$ plates produced by Merck KGaA. Column chromatography was performed with acidic Silica gel 60 (spherical, 40-50 μm) or neutral Silica gel 60N (spherical, 40-50 μm) produced by Kanto Chemicals. Small amounts of solvent were removed using a Smart Evaporator CEV1-SQ-P2 (BioChromato, Kanagawa, Japan).

Optical rotations were measured on a JASCO P-2200 digital polarimeter at the sodium lamp (λ=589 nm) D line and are reported as follows: $[\alpha]_D^T$ (c g/100 mL, solvent). Infrared (IR) spectra were recorded on a JASCO FT-IR 4100 spectrometer and are reported in wavenumbers ($cm^{-1}$). $^1H$ and $^{13}C$ NMR spectra were recorded on a JEOL JNM-EXC 300 spectrometer (300 MHz) or on a JEOL JNM-ECA 500 spectrometer (500 MHz). $^1H$ NMR data are reported as follows: chemical shift (δ, ppm), integration, multiplicity (s, singlet; d, doublet; t, triplet; q, quartet; m, multiplet), coupling constants (J) in Hz, assignments. $^{13}C$ NMR data are reported in terms of chemical shift (δ, ppm). ESI-MS spectra were recorded on a JEOL JMS-T100LC instrument. Mass spectra were reported in terms of mass-to-charge ratio (m/z). HPLC purifications were performed with SHIMADZU LC-6AD, degasser unit DGU-20$A_{3R}$, refractive index detector RID-10A, UV-Vis SPD-20A, valve unit FCV-12AH, and fraction collector FRC-10A.

The carbon numbering on $^1H$ NMR of all compounds is corresponding with desmosine presented by the following Chemical formula 5.

(5)

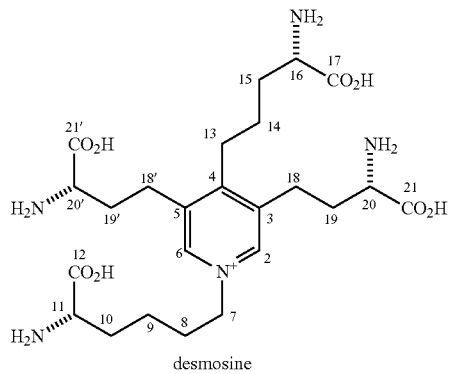

desmosine

Synthesis Example 1

First, the compound represented by the chemical formula 2 shown in Schemes 2 and 3 was synthesized according to the following.

Synthesis Example 1-1

(S)-20-((tert-Butoxycarbonyl)amino)-18-methoxy-21-oxobutanoic acid (9): L-Aspartic acid 7 (5.03 g, 37.8 mmol) was added to methanol (25 mL) and cooled to −30° C. Thionyl chloride (3.7 mL) was added dropwise to the mixture, the cooling bath was removed and the solution was slowly warmed to room temperature. After standing for 25 minutes, diethyl ether (25 mL) was added to the mixture and upon cooling and shaking, the product was precipitated as a white solid which was filtered immediately, washed with ice cold diethylether and collected. The L-aspartic acid methyl ester hydrochloride 8 was obtained as a colorless solid, and was used to the next reaction without further purification.

To a stirred solution of L-aspartic acid methyl ester hydrochloride (5.93 g, 32.3 mmol) in dioxane (120 mL) was added at 0° C. aqueous solution of $Na_2CO_3$ (1 M, 105 mL) followed by $Boc_2O$ (8.25 mL, 35.9 mmol). The reaction mixture was stirred 18 h at 40° C. before being concentrated. The resulting solution was acidified pH 3.0 at 0° C. with 1M HCl and extracted with EtOAc. The combined organic layers were washed with water and dried over $Na_2SO_4$, and concentrated in vacuo. Purification on silica gel column chromatography (MeOH/$CH_2Cl_2$=1/5) afforded the compound 9 as a yellow oil (7.03 g, 28.4 mmol, 81% (2 steps)); Rf 0.64 (MeOH/$CH_2Cl_2$=1:5); $[\alpha]_D^{25}$=+24.9 (c 0.26, $CHCl_3$) (lit value[1]: $[\alpha]_D^{25}$=+23.5 (c 0.26, $CHCl_3$); IR (ATR, $cm^{-1}$) 2982, 1509, 1440, 1394, 1371, 1248, 1048, 848, 782, 608; $^1H$ NMR ($CDCl_3$) δ5.56 (1H, d, J=8.64 Hz, NH), 4.61 (1H, s, H20), 3.72 (3H, s, OMe), 3.10 (1H, dd, J=17.2, 4.5 Hz, H19), 2.85 (1H, dd, J=17.4, 4.9 Hz, H19), 1.45 (9H, s, tBu); $^{13}C$ NMR ($CDCl_3$, 75 MHz) δ174.6, 171.4, 155.5, 51.9, 49.6, 36.3, 28.1, 128.3; ESI-MS (m/z) calcd for $C_{10}H_{17}NO_6$ $[M+H]^+$ 247.11, found 247.17.

Synthesis Example 1-2

(S)-21-tert-Butyl-20-((tert-butoxycarbonyl)amino)-18-hydroxybutanoate (10): A solution of the compound 9 (1.77 g, 7.16 mmol), $BnEt_3NCl$ (1.20 g, 5.26 mmol) and $K_2CO_3$ (4.73 g, 34.19 mmol) in MeCN (10.0 mL) was stirred vigorously at room temperature for 5 h. Then, tBuBr (4.68 mL, 41.7 mmol) was added to the solution and the reaction mixture was warmed to 50° C. and stirred rapidly. After 3 h, additional MeCN was added (6.26 mL) to the solution and the resulting mixture was stirred for 24 h. The aqueous layer was then extracted with EtOAc. The combined organic layers were washed with brine, dried over $Na_2SO_4$, and concentrated in vacuo. Purification on silica gel column chromatography (hexane/EtOAc=9:1) afforded tBu ester 10 as a white solid (1.37 g, 4.51 mmol, 63%); Rf 0.58 (hexane/EtOAc=2:1); $[\alpha]_D^{20}$+15.2 (c 0.026, $CHCl_3$) (lit value[1]: $[\alpha]_D^{20}$+16.7 (c 0.026, $CHCl_3$)); IR (ATR, $cm^{-1}$) 3423, 2981, 1738, 1434, 1407, 1365, 1303, 1070, 1045, 1023, 967, 923, 880, 850, 824, 693, 599; $^1H$ NMR ($CDCl_3$, 300 MHz) δ5.43 (1H, d, J=8.8 Hz, NH), 4.48-4.42 (1H, m, H20), 3.69 (3H, s, OMe), 2.95 (1H, dd, J=16.6, 4.6 Hz, H19), 2.76 (1H, dd, J=16.6, 5.0 Hz, H19), 1.45 (9H, s, tBu), 14.8 (9H, s, tBu); $^{13}C$ NMR ($CDCl_3$, 75 MHz) δ171.2, 169.8, 155.3, 82.1, 79.7, 51.7, 50.4, 36.8, 28.2, 27.7; ESI-HRMS (m/z) calcd for $C_{14}H_{20}NaO_6$ [M+Na]+ 326.1580, found 326.1571.

Synthesis Example 1-3

(S)-21-tert-Butyl-20-((tert-butoxycarbonyl)amino)-18-oxobutanoic acid (11): To a solution of tBu ester 10 (1.65 g, 5.44 mmol) in MeOH (3.45 mL) was added 2M NaOH (2.47 mL). After stirring at room temperature for 3 h, MeOH was removed at reduced pressure and the remaining aqueous layer washed with ether. The aqueous layer was then acidified to pH 2 with 1M HCl and extracted with EtOAc. The combined organic layers were washed with brine, dried over $Na_2SO_4$, and concentrated in vacuo. Purification on silica gel column chromatography (hexane/EtOAc=3/1) afforded the compound 11 as a colorless solid (1.48 g, 5.11 mmol, 940); $[\alpha]_D^{22}$ −26.7 (c 1.5, MeOH) (lit value[2]: $[\alpha]_D^{22}$ −24.3 (c 1.5, MeOH)); IR (ATR, cm$^{-1}$) 3424, 2980, 1738, 1501, 1434, 1407, 1365, 1338, 1303, 1222, 1069, 1045, 1022, 969, 923, 879, 849, 825, 694, 600, 569; $^1$H NMR (CDCl$_3$, 300 MHz) δ5.44 (1H, d, NH), 4.44 (1H, m, H20), 3.03 (2H, dd, J=18.5, 4.6 Hz, H19), 2.82 (2H, dd, J=17.2, 5.02 Hz, H19), 1.45 (9H, s, tBu), 1.45 (9H, s, tBu); $^{13}$C NMR (CDCl$_3$, 75 MHz) δ176.7, 176.3, 169.9, 155.4, 82.5, 80.3, 51.8, 50.3, 36.8, 28.3, 27.8; ESI-MS (m/z) calcd for $C_{13}H_{23}NNaO_6$ [M+Na]+ 312.14, found 312.17.

Synthesis Example 1-4

(S)-21-tert-Butyl 20-((tert-butoxycarbonyl)amino)-18-hydroxybutanoate (12): To a solution of the compound 11 (1.52 g, 5.26 mmol) in THF (25.8 mL) cooled to −15° C. was added N-methylmorpholine (0.64 mL, 5.79 mmol) and EtOCOCl (0.55 mL, 5.79 mmol). After stirring at −15° C. for 1 h, the precipitated N-methylmorpholine hydrochloride was removed by filtration and washed with THF (12.5 mL). The filtrate cooled to 0° C. was added NaBH$_4$ (0.298 g, 7.89 mmol), followed by the dropwise addition of water (5.17 mL). After stirring at 0° C. for 0.5 h, the reaction mixture was quenched with saturated NH$_4$Cl solution. The aqueous layer was then extracted with EtOAc. The combined organic layers were washed with brine, dried over Na$_2$SO$_4$, and concentrated in vacuo. The alcohol 12 was obtained as a white solid (1.17 g, 4.26 mmol, 81%); Rf 0.30 (hexane/EtOAc=2:1); $[\alpha]_D^{20}$ −39.3 (c 1.0, EtOH) (lit value[2]: $[\alpha]_D^{22}$ −37.5 (c 1.5, EtOH)); IR (ATR, cm$^{-1}$) 3384, 2978, 1697, 1506, 1392, 1366, 1246, 1050, 994, 848, 738, 650, 593, 580, 563; $^1$H NMR (CDCl$_3$, 300 MHz) δ5.33 (1H, d, J=6.6 Hz, NH), 4.37-4.32 (1H, m, H20), 3.75-3.59 (2H, m, H19), 2.18-2.09 (1H, m, H18), 1.56-1.53 (1H, m, H19), 1.47 (9H, s, tBu), 1.45 (9H, s, tBu); $^{13}$C NMR (CDCl$_3$, 75 MHz) δ171.9, 171.1, 156.5, 82.1, 80.1, 62.0, 58.2, 50.9, 36.3, 28.2, 27.9; ESI-MS (m/z) calcd for $C_{13}H_{23}NNaO_5$ [M+Na]+ 298.16, found 298.19.

Synthesis Example 1-5

(S)-21-tert-Butyl-20-((tert-butoxycarbonyl)amino)-18-iodobutanoate (6): Triphenylphosphine (325 mg, 1.24 mmol, 2.0 eq) and imidazole (84.4 mg, 1.24 mmol, 2.0 eq) were dissolved in CH$_2$Cl$_2$ (1.88 mL) with stirring. Iodine (314.7 mg, 1.24 mmol, 2.0 eq) was added to the solution at 0° C. Then, the solution was warmed to room temperature with stirring for 10 min, and was cooled to 0° C. A solution of the compound 12 (170.8 mg, 0.62 mmol, 1.0 eq) in CH$_2$Cl$_2$ (1.88 mL) was also added to the cooled solution. After stirring at 0° C. for 2 h, the reaction mixture filtered through a short column of neutral silica gel eluting with hexane/Et$_2$O (=1:1, ca. 300 mL) and the filtrate was concentrated in vacuo. Purification on silica gel column chromatography (hexane/EtOAc=5:1) afforded the compound 6 as a colorless solid (178.4 mg, 0.46 mmol, 75%); Rf 0.30 (hexane/EtOAc=5:1); $[\alpha]_D^{20}$ −32.2 (c 1.0, MeOH); IR (ATR, cm$^{-1}$) 3396, 2977, 1748, 1423, 1390, 1366, 1349, 1286, 1046, 1023, 990, 954, 901, 864, 847, 700, 640; $^1$H NMR (CDCl$_3$, 300 MHz) δ5.07 (1H, s, NH), 4.22-4.16 (1H, m, H20), 3.21-3.16 (2H, m, H19), 2.42-2.34 (1H, m, H18), 2.20-2.00 (1H, m, H19), 1.48 (9H, s, tBu), 1.46 (9H, s, tBu); $^{13}$C NMR (CDCl$_3$, 75 MHz) δ171.0, 155.8, 82.9, 80.4, 55.4, 38.0, 28.7, 28.4, −7.69; ESI-MS (m/z) calcd for $C_{13}H_{24}INNaO_4$ [M+Na]+ 408.06, found 408.04.

Synthesis Example 1-6

(2S,2'S)-tert-Butyl-4,4'-(4-(S)-5-(tert-butoxy)-4-(tert-butoxycarbonylamino)-5-oxopent-1-ynyl)pyridine-3,5-diyl) bis(2-(tert-butoxycarbonylamino)butanoate)) (3) and 3-bromo-(2S,2'S)-tertbutyl-4,4'-(4-(S)-5-(tert-butoxy)-4-(tert-butoxycarbonylamino)-5-oxopent-1-ynyl)pyridine-5-yl)-2-(tert-butoxycarbonylamino)butanoate (14): Zinc dust (200 mg, 3.0 mmol, 30 eq) was placed in a nitrogen-purged 1.5 mL microtube. Dry DMF (150 μL) and trimethylsilyl chloride (60 μL, 0.47 mmol) were added, and the resulting mixture was stirred vigorously for 15 min at room temperature. Stirring was stopped, and the solution was removed by micro syringe. The remaining solid was dried using a hot air gun at reduced pressure. The activated zinc was cool to room temperature, and a solution of (S)-21-tert-butyl-20-((tert-butoxycarbonyl)amino)-18-iodobutanoate 6 (192.3 mg, 0.495 mmol, 5.0 eq) in dry DMF (150 μL and rinsed with 100 μL DMF) was added to the activated zinc. The reaction mixture was stirred at room temperature for 1 h, after which time TLC analysis (hexane/ethyl acetate=5/1) revealed that no starting material remained. Stirring was stopped and the zinc duct was allowed to settle using a centrifuge separator. The solution was removed from the activated zinc via micro syringe with 200 μL DMF and add to a 10 mL flask, containing PEPPSI (pyridine enhanced precatalyst preparation, stabilization, and initiation)-IPr (13.5 mg, 20 mol %) and the compound 5 (50.1 mg, 0.098 mmol, 1.0 eq). Stirring was continued for 6 h at 40 and 18 h at 50° C., the reaction mixture was diluted with ethyl acetate and quenched with a saturated NH$_4$Cl solution. The aqueous layer was then extracted with EtOAc. The combined organic layers were washed with brine, dried over Na$_2$SO$_4$, and concentrated in vacuo to give the crude product as yellow oil. Purification by flash column chromatography (hexane/EtOAc=1/2→1/5) afforded the compound 3 (50.0 mg, 0.058 mmol, 59%) as a yellow oil and 14 (31%) as a yellow oil, respectively. 3: Rf 0.19 (hexane/EtOAc=1:2); $^1$H NMR (300 MHz, CDCl$_3$) 8.30 (2H, s, H2/6), 6.10 (1H, s, NH), 5.49 (2H, d, J=7.16 Hz, NH), 4.48 (1H, m, H16), 4.33 (2H, m, H20/20'), 3.16-3.01 (2H, m, H15), 2.80-2.75 (4H, m, H18/18'), 2.12-2.08 and 1.97-1.90 (4H, m, H19/19'), 1.45 (54H, s, tBu); ESI-HRMS (m/z) calcd for $C_{45}H_{72}N_4NaO_{12}$ [M+Na]+: 883.5015, found: 883.5044. 14: Rf 0.19 (hexane/EtOAc=1:2); $^1$H NMR (300 MHz, CDCl$_3$); 8.56 (1H, s, H2), 8.37 (1H, s, H6), 5.78 (1H, d, J=6.65 Hz, NH), 5.46 (1H, d, J=7.44 Hz, NH) 4.47-4.43 (1H, m, H16), 4.33-4.30 (1H, m, H20), 3.10-3.01 (2H, m, H15), 2.85-2.73 (2H, m, H18), 2.16-2.07 and 1.98-1.87 (2H, m, H19), 1.45 (36H, s, tBu); ESI-HRMS (m/z) calcd for $C_{32}H_{48}BrN_3NaO_8$ [M+Na]+: 704.2523, found: 704.2528.

Synthesis Example 1-7

(3,5-Bis((S)-4-(tert-butoxy)-3-(tert-butoxycarbonylamino)-4-oxobutyl)-4-((S)-5-(tert-butoxy)-4-(tert-butoxycarbonylamino)-5-oxopent-1-ynyl)-1-((S)-6-(benzyloxy)-5-(tert-butoxycarbonylamino)-6-oxohexyl) pyridinium iodide) (2): A mixture of 3 (60.0 mg, 69.7 µmol, 1.0 eq) and 11-[bis-(tert-butoxycarbonyl)-amino]-7-iodohexanoic acid tert-butyl ester 4 (71.7 mg, 139.7 µmol, 3.0 eq) in MeNO$_2$ (1.89 mL) was stirred at 60° C. for 15 h to 65° C. for 30 h. The reaction mixture was concentrated in vacuo. Purification on silica gel column chromatography (CH$_2$Cl$_2$/MeOH=1:1) afforded the compound 2 (89.7 mg, 65.5 µmol, 94%) as a yellow oil; Rf 0.56 (CH$_2$Cl$_2$/MeOH=1:1); $[\alpha]_D^{20}$ +16.1 (c 0.1, CH$_3$Cl); IR (ATR, cm$^{-1}$) 2979, 1713, 1497, 1366, 1252, 1153, 849, 753; $^1$H NMR (300 MHz, CDCl$_3$); 9.03 (2H, s, H2/6), 6.10 (1H, s, NH), 5.62 (2H, s, NH), 4.81 (2H, m, H7), 4.77-4.72 (1H, m, H20), 4.66-4.64 (1H, m, H20'), 4.48 (1H, s, H16), 4.24-4.20 (1H, m, H11), 3.34-3.30 (2H, m, H15), 3.00-2.88 (4H, m, H18), 2.25-2.10 (6H, m, H8/9/10), 1.74-1.69 (4H, m, H19), 1.48 (81H, s, tBu); $^{13}$C NMR (CDCl$_3$, 125 MHz); 6171.0, 169.6, 169.2, 155.8, 152.6, 143.4, 141.5, 83.1, 82.5, 81.5, 80.4, 79.9, 61.8, 58.3, 53.5, 52.8, 31.6, 31.1, 28.4, 28.3, 28.1, 28.0, 27.9, 24.7, 23.2, 22.7, 14.1; ESI-HRMS (m/z) calcd for C$_{65}$H$_{108}$N$_5$O$_{18}$ [M]$^+$ 1246.7689, found 1246.7677.

Synthesis Example 2

The compound represented by the chemical formula (1) was synthesized according to Scheme 2.

4-(16-(S)-Amino-16-carboxy-butyl)-1-(11-(S)-amino-11-carboxy-pentyl)-3,5-bis-(20-(S)-amino-20-carboxy-[D$_4$]propyl)-pyridinium, Desmosine-d$_4$ (1-d$_4$): [Without D-H exchange] A solution of the compound 2 (10.0 mg, 7.3 µmol, 1.0 eq) in CD$_3$OD (0.26 mL) was treated with 10% Pd/C (42.4 mg, 36.5 mmol, 5.0 eq) and under D$_2$ atmosphere deuterated using a balloon at room temperature. After stirring for 6 days at room temperature, the reaction mixture was separated by filtration through a Celite pad on neutral silica gel eluting with MeOH and the filtrate was then concentrated in vacuo to afford crude mixture of deuterated pyridinium salt as yellow solid (3.6 mg, 2.6 µmol). The obtained product was used to the next reaction without further purification.

A mixture of TFA and distilled H$_2$O (7.0 mL, TFA/H$_2$O=95/5) was added to the crude deuterated pyridinium salt (3.6 mg, 2.6 µmol, 1.0 eq) at room temperature and stirred for 3 h. The solvent was removed in vacuo. The crude product was purified by reversed phase HPLC. The conditions were as follows; column: Cosmosil 5C$_{18}$-AR-II (10× 250 mm, Nacalai Tesque, Kyoto); solvent (A: MeCN with 0.1% TFA, B: H$_2$O with 0.1% TFA): A/B=2/98 (0-3 min), A/B=2-5/98-95 (3-13 min), A/B=5/95 (13-15 min), A/B=5-2/98-95 (15-17 min), A/B=2/98 (17-20 min); flow rate: 3.0 mL min$^{-1}$; detection: 278 nm; temperature: 40° C.; R$_t$=4.9 min. As a result, desmosine-d$_4$ 1-d$_4$ was obtained as a yellow solid (1.8 mg, 2.8 µmol, 38% (2 steps)); Rf 0.22 [MeOH (0.1% TFA)/H$_2$O (0.1% TFA)=1:9]; $^1$H NMR (D$_2$O, 500 MHz) 58.55 (2H, s, H2/6), 4.52 (2H, m, J=6.9 Hz, H7), 3.92 (2H, m, H20/20'), 3.88-3.78 (1H, m, H16), 3.88-3.78 (1H, m, H11), 3.08-2.87 (4H, m, H18/18'), 2.20-2.19 (4H, m, H19/19'), 2.08-2.02 (2H, m, H15), 1.93-1.91 (4H, m, H8/10), 1.52-1.38 (2H, m, H9); ESI-MS (m/z) calcd for C$_{24}$H$_{36}$D$_4$N$_5$O$_8$[M]$^+$ 530.3128, found 530.3145 (d$_4$=55%, d$_3$=370, d$_2$=8%).

Example 1

The compound represented by the chemical formula (1) was synthesized according to Scheme 3.

4-(16-(S)-Amino-16-carboxy-butyl)-1-(11-(S)-amino-11-carboxy-pentyl)-3,5-bis-(20-(S)-amino-20-carboxy-[D$_4$]propyl)-pyridinium, Desmosine-d$_4$ (1-d$_4$): [With D-H exchange] A solution of the compound 2 (19.1 mg, 13.9 µmol, 1.0 eq) was dissolved in CD$_3$OD (126 µL) and the solvent was removed in vacuo. This manipulation was repeated five times and deuterated 2' was obtained. A solution of the compound 2' (19.3 mg, 14.0 µmol, 1.0 eq) in CD$_3$OD (0.53 mL) was treated with 10% Pd/C (80.4 mg, 75.8 µmol, 5.0 eq) and under D$_2$ atmosphere deuterated using a balloon at room temperature. After stirring for 6 days at room temperature, the reaction mixture was separated by filtration through a Celite pad on neutral silica gel eluting with MeOH and the filtrate was then concentrated in vacuo to afford crude mixture of deuterated pyridinium salt as yellow solid (15.3 mg, 11.0 µmol). The obtained product was used to the next reaction without further purification.

A mixture of TFA and distilled H$_2$O (2.8 mL, TFA/H$_2$O=95/5) was added to the crude deuterated pyridinium salt (15.3 mg, 11.0 µmol, 1.0 eq) at room temperature and stirred for 3 h. The solvent was removed in vacuo. The crude product was purified by reversed phase HPLC. Desmosine-d$_4$ 1-d$_4$' was obtained as a yellow solid (9.4 mg, 14.6 µmol, quant (2 steps)); Rf 0.22 [MeOH (0.1% TFA)/H$_2$O (0.1% TFA)=1:9]; $^1$H NMR (D$_2$O, 500 MHz) 58.56 (2H, s, H2/6), 4.79-4.49 (2H, t, J=6.9 Hz, H7), 4.16-4.14 (2H, m, H20/20'), 4.06-4.00 (1H, m, H16), 4.04-3.97 (1H, m, H11), 3.09-2.90 (4H, m, H18/18'), 2.28-2.22 (4H, m, H19/19'), 2.11-1.95 (6H, m, H8/10/15), 1.52-1.42 (2H, m, H9); $^{13}$C NMR (D$_2$O, 125 MHz); 6174.7, 174.5, 144.7, 142.7, 63.4, 32.1, 32.8, 32.6, 32.1, 28.6, 24.0; ESI-MS (m/z) calcd for C$_{24}$H$_{36}$D$_4$N$_5$O$_8$ [M]+530.313, found 530.318 (d$_4$=88%, d$_3$=12%).

According to the process of the present example, a yield of Desmosine-d$_4$ was improved compared with that of Synthesis Example 2.

In the present specification, the following abbreviations were employed.

Ac: acetyl

Bn: benzyl

Bu: butyl

DMF: dimethylformamide

Et: ethyl

IPr: isopropyl

Me: methyl

THF: tetrahydrofuran rt: room temperature h: hour d: day

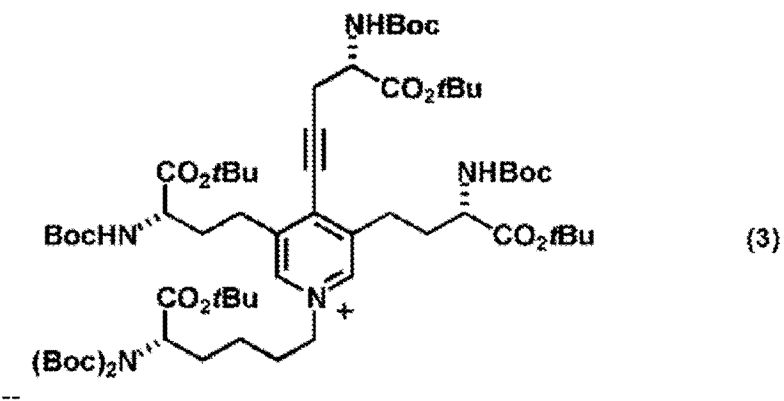

What is claimed is:

1. A process for preparing a compound represented by the following formula (1) or a salt thereof:

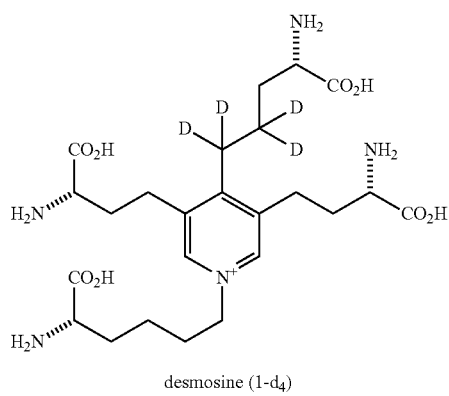

desmosine (1-d₄)

(wherein in the formula (1), one, or two or more of hydrogen atom may be substituted with their) isotope, the process comprising exchanging one or more of an amino proton in a compound represented by the following formula (2) or a salt thereof to deuterium:

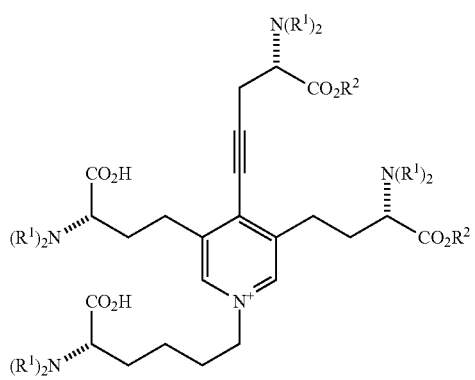

(wherein in the formula (2), each of $R^1$ is independently hydrogen atom, tert-butyloxycarbonyl group or benzyloxycarbonyl group, and $R^2$ is independently tert-butyl group, benzyl group, methyl group or ethyl group), group, and after the exchanging, converting a deuterium-exchanged compound of the compound represented by the formula (2) or a salt thereof into the compound represented by the formula (1) or a salt thereof.

2. The process according to claim 1, wherein the exchanging comprises one or more cycle of dissolving the compound represented by the formula (2) in a solvent comprising deuterated polar protic solvent and removing the solvent.

3. The process according to claim 2, wherein the solvent is deuterated methanol.

4. The process according to claim 1, wherein the converting comprises reducing the deuterium-exchanged compound or a salt thereof with deuterium gas and palladium carbon.

5. The process according to claim 1, wherein the compound represented by the formula (2) is the compound represented by the following formula (3) or (4):

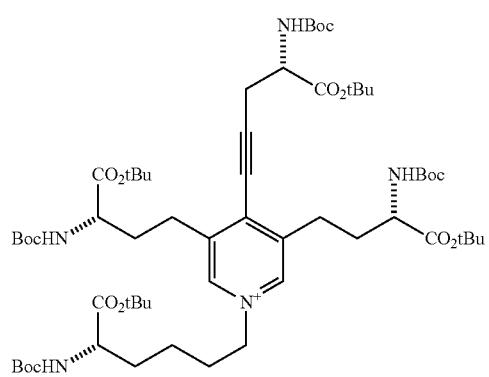

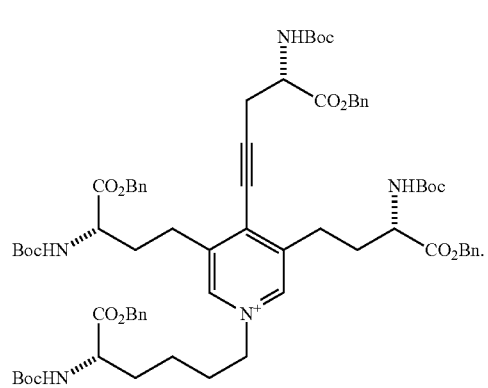

6. A process, comprising:
Step 1: one or more cycles of dissolving a compound represented by the following formula (2) or a salt thereof in a solvent comprising deuterated polar protic solvent and removing the solvent; and
Step 2: reducing the compound obtained in Step 1 with deuterium gas and palladium carbon,

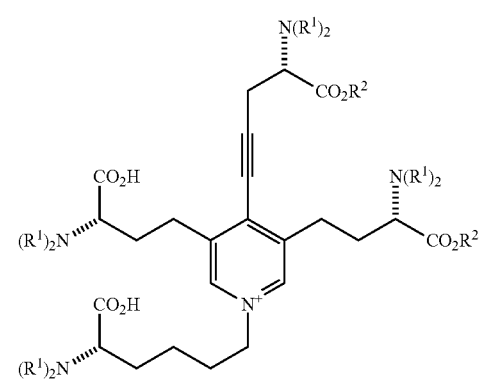

wherein, in the formula (2), each of $R^1$ is independently hydrogen atom, tert-butyloxycarbonyl group or benzyloxycarbonyl group, and $R^2$ is independently tert-butyl group, benzyl group, methyl group or ethyl group.

7. The process according to claim 6, wherein the solvent is deuterated methanol.

8. The process according to claim 6, wherein the compound represented by the formula (2) is the compound represented by the following formula (3) or (4):

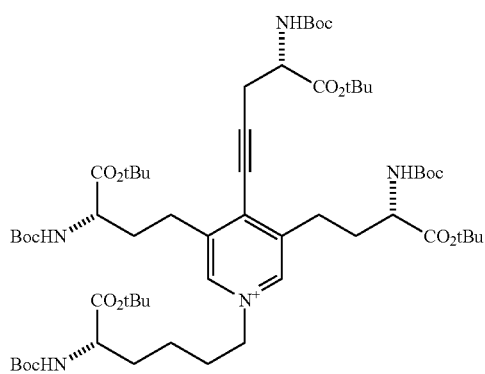

(3)

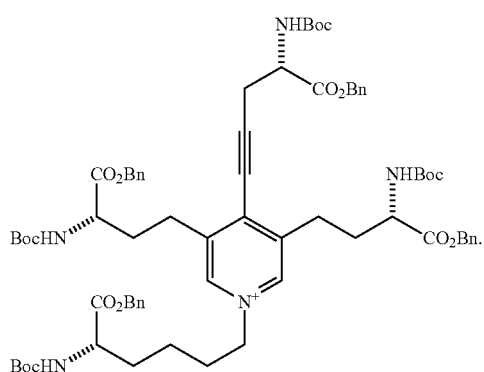

(4)

9. The process according to claim 6, wherein Step 2 is a deuterium addition reaction to the carbon-carbon triple bond of the compound obtained in Step 1.

10. The process according to claim 6, wherein two or more cycles of Step 1 are performed.

11. The process according to claim 6, wherein three or more cycles of Step 1 are performed.

12. The process according to claim 2, wherein the exchanging comprises two or more cycles of dissolving the compound represented by the formula (2) in the solvent comprising deuterated polar protic solvent and removing the solvent.

13. The process according to claim 2, wherein the exchanging comprises three or more cycles of dissolving the compound represented by the formula (2) in the solvent comprising deuterated polar protic solvent and removing the solvent.

* * * * *

UNITED STATES PATENT AND TRADEMARK OFFICE
CERTIFICATE OF CORRECTION

PATENT NO. : 10,280,143 B1
APPLICATION NO. : 15/810634
DATED : May 7, 2019
INVENTOR(S) : Toyonobu Usuki Page 1 of 2

It is certified that error appears in the above-identified patent and that said Letters Patent is hereby corrected as shown below:

In the Specification

Column 4, Lines 50–65; Delete formula (3) and insert the following formula (3):

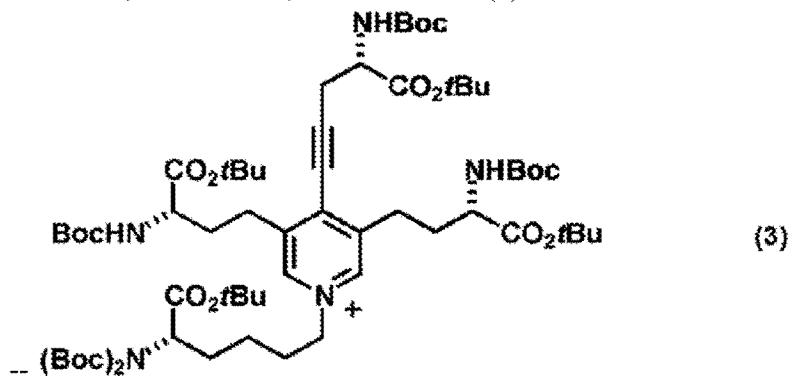

Column 8, Lines 1–12; The unlabeled intermediate compound to the left of the reaction arrow should be labeled --14 (31%)--

Column 8, Lines 23–37; The final product 1-$d_4$ of Scheme 2 and its yield are missing and should appear as follows:

Signed and Sealed this
Twenty-second Day of October, 2019

Andrei Iancu
*Director of the United States Patent and Trademark Office*

CERTIFICATE OF CORRECTION (continued)
U.S. Pat. No. 10,280,143 B1

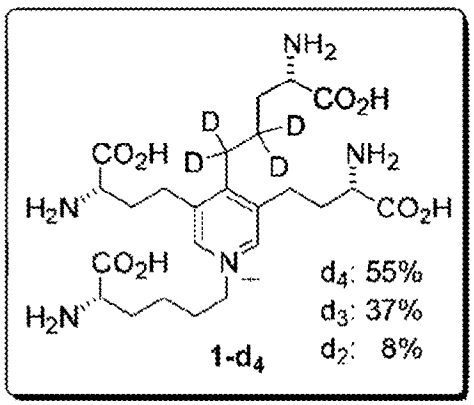

Column 8, Line 60; Delete "MeOH-d⁴" and insert --MeOH-$d_4$--

Column 9, Lines 1–17; The final product 1-$d_4$' of Scheme 3 and its yield are missing and should appear as follows:

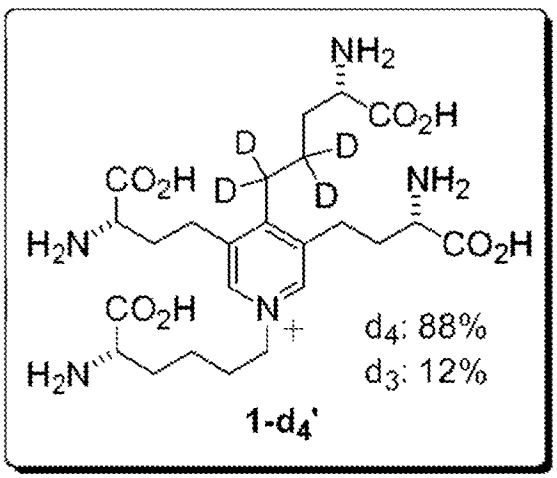

In the Claims

Claim 5, Column 16, Lines 6–24 and Claim 8, Column 17, Lines 19–33; Delete both instances of formula (3) and insert the following formula (3):